United States Patent [19]
Edwards

[11] Patent Number: 5,902,294
[45] Date of Patent: May 11, 1999

[54] VALVE FOR URINE DRAINAGE APPLICATIONS

[75] Inventor: John Victor Edwards, Reigate, United Kingdom

[73] Assignee: Salt & Son Limited, Birmingham, United Kingdom

[21] Appl. No.: 08/732,432
[22] PCT Filed: Apr. 27, 1995
[86] PCT No.: PCT/GB95/00970
§ 371 Date: Mar. 10, 1997
§ 102(e) Date: Mar. 10, 1997
[87] PCT Pub. No.: WO95/29651
PCT Pub. Date: Nov. 9, 1995

[30] Foreign Application Priority Data

Apr. 29, 1994 [GB] United Kingdom ................... 9408567

[51] Int. Cl.[6] .................................. A61F 5/44; F16K 5/00
[52] U.S. Cl. ......................... 604/327; 604/350; 604/349; 251/287; 251/310
[58] Field of Search .................................. 251/287, 310; 604/349–353, 327, 329

Primary Examiner—Robert A. Clarke
Attorney, Agent, or Firm—Ivah H. Donner, Pepper Hamilton LLP; Suresh Koshy, Pepper Hamilton LLP

[57] ABSTRACT

A valve for urine drainage applications has a valve housing for attachment to a urine receptacle and a valve member rotatable within the valve housing between an open position, in which liquid can flow from the receptacle along an angled path from the inlet to the outlet from the valve, and a closed position cutting off the liquid flow. The valve member can be rotated about an axis substantially normal to the direction of liquid outflow from the valve and a manually operable tab or handle is provided for rotating the valve member in the housing and is arranged to point in the direction of the outflow from the valve when the valve member is in the open position.

7 Claims, 1 Drawing Sheet

VALVE FOR URINE DRAINAGE APPLICATIONS

RELATED APPLICATIONS

This is a national stage application, claiming priority to international application PCT GB95/00970, which was filed on Apr. 27, 1995.

FIELD OF THE INVENTION

This invention relates to a valve for urine drainage applications, particularly for a urostomy pouch.

SUMMARY OF THE INVENTION

It is an object of the invention to provide a valve which is easy end intuitive to use and which can be made substantially leak-free on a production basis.

From one aspect, the invention provides a valve for urine drainage applications having a valve housing for attachment to a urine receptacle and a valve member rotatable within the valve housing between an open position, in which liquid can flow from the receptacle along an angled path to the outlet from the valve, and a closed position cutting off the liquid flow, wherein the valve member can rotate about an axis substantially normal to the direction of liquid outflow from the valve when the valve member is rotated to the open position and wherein a manually operable means for rotating the valve member in the housing is arranged to point in the direction of the flow from the valve when the valve member is in the open position. Preferably, the valve is mounted on the receptacle so that the direction of liquid outflow is downwards when the receptacle is being worn in use.

From another aspect, the invention provides a valve for a urostomy pouch, comprising a body member and a valve member, the body member having an attachment surface for attaching to a wall of the pouch, and a housing containing a cylindrical bore for receiving the valve member and which communicates with the pouch via an aperture in the attachment surface, said housing also having an outlet, and said valve member comprising a cylinder having a manually operable handle extending therefrom, whereby said valve member can be rotated from an open position, in which the handle points in the same direction as the outlet, and in which position liquid from the pouch can flow through an angled path from the aperture into the bore and a further angled path from the bore to the outlet; to a closed position, in which the handle points away from the outlet, and the valve member seals the outlet from the aperture.

The attachment surface may be formed by one side of a plate-like member which carries the housing an its other side. Advantageously, the housing is substantially cylindrical and is closed at one end where the aperture is located and open at the other end where the handle of the valve member protrudes.

The cutlet preferably comprise a tube pointing downwards when the pouch is being worn and forms a T-shape in conjunction with the housing.

The up ad down operating movement of the handle is more ergonomic than the sideways operation of valves in current use. Also, a downward movement of the handle intuitively indicates to the patient opening of the valve, whilst upward movement intuitively indicates closing, even when this valve is in such a position that it is beyond the patient's line at sight.

BRIEF DESCRIPTION OF THE DRAWINGS

The invention will now be described by way of example with reference to the accompanying drawings, in which.

DETAILED DESCRIPTION OF THE INVENTION

Figure 1:
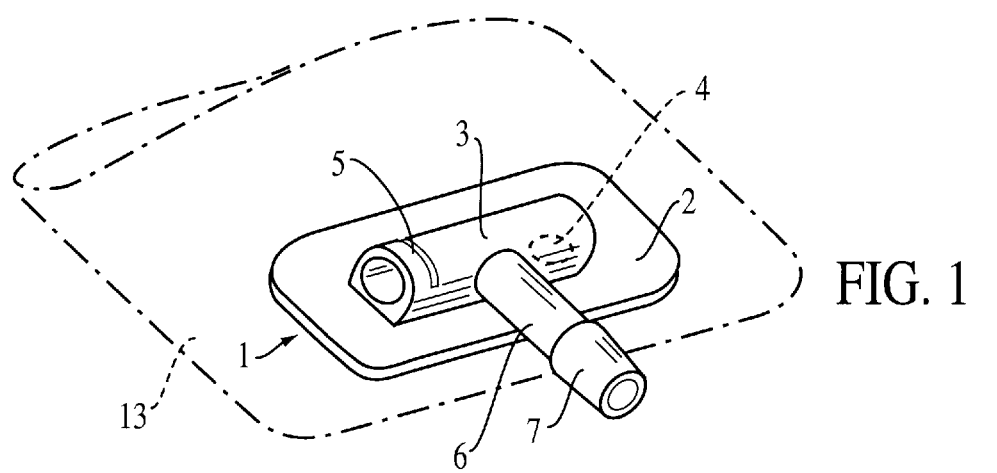
FIG. 1 is a front perspective view of one embodiment of the valve housing or body member.
Figure 2:
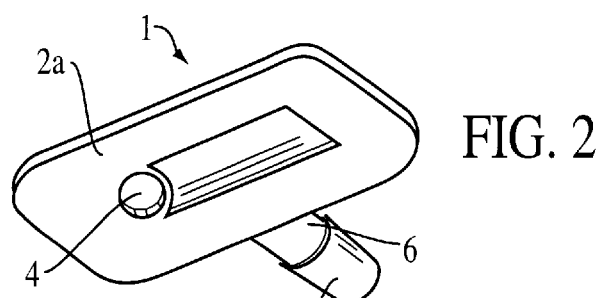
FIG. 2 is a rear perspective view of the valve housing or body member shown in FIG. 1.
Figure 4:
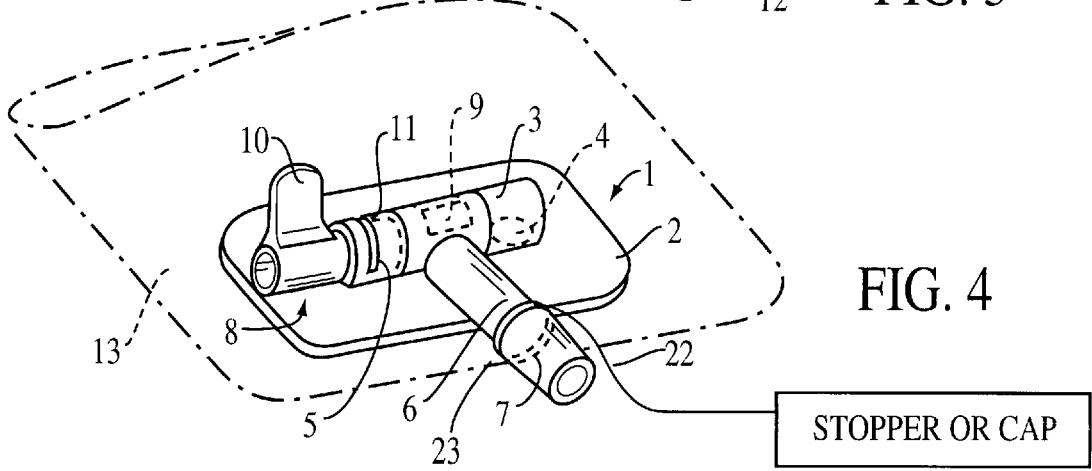
FIG. 4 is a perspective view of a valve assembled from the members shown in FIGS. 1 to 3.

Referring to the drawings, the valve housing or body member generally indicated at 1 includes a substantially rectangular attachment plate 2 having a surface 2a which can be sealed on to the side wall of a urostomy pouch 13 indicated in broken lines in FIGS. 1 and 4. The attachment plate 2 carries a substantially cylindrical housing 3 which is open at one end and closed at the other end. Adjacent the closed end of the housing 3, an inlet aperture 4 in the plate 2 allows communication between the interior of the housing and the pouch. A slot 5 is provided in the wall of the housing 3 adjacent its opens end, whose purpose will be described later.

The outlet 6 from the valve consists of a tube communicating with the interior of the housing 3 and extending outwardly therefrom at an intermediate position between its ends thereof. The outlet 6 terminates in a tapered section 7 to which a drainage attachment can be connected if desired.

Figure 3:
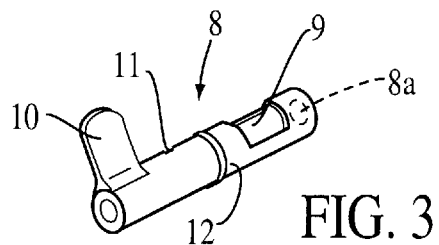
FIG. 3 is a perspective view of one embodiment of the valve member for cooperation with the valve housing or body member.

FIG. 3 shows the valve member 8 which is located within the housing 3 and is of cylindrical form. One end of the valve member is open as shown at 8a to allow communication between the inlet aperture and a hollow part of the valve member having an aperture 9 which extends over almost half the circumstances of the cylinder. A manually operable tab or handle 10 extends normally to the member 8 adjacent its other end, whilst a small lug 11 is also located on the outside of the member 8 near the handle 10 and at the same circumferential position.

FIG. 4 shows the valve assembled from the members 1 and 3, with the lug 11 engaged in the slot 5 to locate and retain the valve member 8 in position. FIG. 4 shows the operating member 8 half-way between the open and closed position. In order to close the valve, the handle 10 is moved upwardly as viewed in FIG. 4 so that the aperture 9 is disposed away from the outlet 6 which is then closed by a portion of the cylindrical wall of the member 8. When the handle 10 is moved downwardly as viewed in FIG. 4, the valve member 8 is rotated through approximately 180° to bring the aperture 9 opposite the outlet 6 and thereby provide a liquid outflow passage from the pouch through the apertures 4, 8a, 9 and 6. It will be noted that the liquid is caused to change direction twice during its passage to the outlet, namely once between the apertures 4 and 8a and again between the apertures 9 and 6 and this extended flow path helps to render the valve leak-free.

The surface 2a of the attachment plate 2 can easily be sealed to the side of a urostomy pouch 13, unlike many of the currently used products in which a tap protrudes from the bottom of the pouch and which have a propensity to leak around the seal between the tap and the pouch film.

The invention, as exemplified by the embodiment described above, provides a simple and ergonomic valve for a urostomy pouch. The long path length between the inlet aperture 4 and the outlet 6 helps to render the valve leak-free on a mass production basis.

Modifications many be made to the specific embodiment described without departing from the scope of the invention. For example, an O ring 12 may be provided in a groove around the surface of the operating member 8 between the lug 11 and the aperture 9, to improve still further the seal between the members 1, 8. The surface of the lug 11 facing the aperture 9 may be inclined towards the surface of the operating member 8 to facilitate insertion thereof into the housing 3.

Additionally, a stopper or cap may be provided for closing the end of the outlet 6. The stopper may be connected by a flexible strap 22 to a ring 23 surrounding the outlet 6 and retained thereon by the upper edge of the tapered section 7, in order to prevent less of the stopper when it is unplugged from the outlet. The surface of the handle 10 may be dimpled or otherwise textured to give an improved grip.

The parts may also have a shape and configuration different from that specifically described.

I claim:

1. A valve for a urostomy pouch having a side surface, said valve comprising:

a valve housing including means for attachment to the side surface;

a valve inlet positioned to receive urine from the pouch;

a valve outlet; and a valve member manually rotatable within the valve housing between an open position, wherein said valve member defines an angled path for liquid outflow from the pouch to the valve outlet, and a closed position, wherein said valve member cuts off the liquid outflow, said valve member rotatable about an axis substantially normal to a direction of the liquid outflow, when said valve member is rotated to said open position, said valve outlet including a tube forming a T-shape with said valve housing, said valve member being generally cylindrical and including a handle for rotation thereof relative to said valve housing, said valve outlet, and said means for attachment between said open and closed positions, said handle, in said open position, pointing in a substantially same direction as said outlet.

2. The valve according to claim 1, wherein said means for attachment includes a plate-like member having first and second sides, said plate-like member including an attachment surface on said first side and carrying said valve housing on said second side.

3. The valve according to claim 1, wherein said valve housing is substantially cylindrical and includes a closed end and an open end, said valve inlet being located at said closed end, said handle protruding from said open end.

4. The valve according to claim 1, further comprising one of an O-ring and a sealing member, encircling said valve member to improve a seal between said valve member and said valve housing.

5. The valve according to claim 1, further comprising a lug, on said valve member, retaining said valve member in said valve housing, said valve housing defining a slot, said lug engaged in said slot.

6. The valve according to claim 1, further comprising:

one of a stopper and a cap for closing said valve outlet, said valve outlet having an end;

means for retaining said one of a stopper and a cap on said valve outlet, when said one of a stopper and a cap is removed from said end of said valve outlet.

7. A urostomy pouch having a side surface and an interior, said urostomy pouch comprising:

a valve including:

a valve housing including means for attachment to the side surface;

a valve inlet positioned to receive urine from the pouch;

a valve outlet; and a valve member manually rotatable within the valve housing between an open position, wherein said valve member defines an angled path for liquid outflow from the pouch to the valve outlet, and a closed position, wherein said valve member cuts off the liquid outflow, said valve member rotatable about an axis substantially normal to a direction of the liquid outflow, when said valve member is rotated to said open position, said valve outlet including a tube forming a T-shape with said valve housing, said valve member being generally cylindrical and including a handle for rotation thereof relative to said valve housing, said valve outlet, and said means for attachment between said open and closed positions, said handle, in said open position, pointing in a substantially same direction as said outlet, wherein said valve is secured to the side surface, said valve inlet communicating with the interior of said pouch, said valve outlet pointing downwards, when said pouch is worn.

* * * * *